(12) United States Patent  
LeMay et al.

(10) Patent No.: US 9,662,249 B2  
(45) Date of Patent: *May 30, 2017

(54) ERGONOMIC TAMPON APPLICATOR

(71) Applicant: Edgewell Personal Care Brands, LLC, Chesterfield, MO (US)

(72) Inventors: Jessica LeMay, Paramus, NJ (US); Kathryn Bennett, Fairfield, CT (US); Keith Edgett, Ramsey, NJ (US); Dane Jackson, Bloomingdale, NJ (US); Mario Turchi, Tenafly, NJ (US); Susanne Weber, New York, NY (US)

(73) Assignee: Edgewell Personal Care Brands, LLC., Chesterfield, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/188,032

(22) Filed: Jun. 21, 2016

(65) Prior Publication Data

US 2016/0296381 A1  Oct. 13, 2016

Related U.S. Application Data

(63) Continuation of application No. 14/576,473, filed on Dec. 19, 2014, which is a continuation of application (Continued)

(51) Int. Cl.  
*A61F 13/20* (2006.01)  
*A61F 13/26* (2006.01)

(52) U.S. Cl.  
CPC ............ *A61F 13/266* (2013.01); *A61F 13/26* (2013.01); *A61F 13/2077* (2013.01); *A61F 13/263* (2013.01); *Y10S 604/904* (2013.01)

(58) Field of Classification Search  
CPC ...... A61F 13/51113; A61F 2013/51117; A61F 13/26; A61F 13/263; A61F 13/266; A61F 13/34; A61F 13/2077  
(Continued)

(56) References Cited

U.S. PATENT DOCUMENTS 1,191,736 A  7/1916  Roberson  
1,218,478 A  3/1917  Sappington  
(Continued)

FOREIGN PATENT DOCUMENTS

AU  8774659  1/1988  
BE  667613  1/1966  
(Continued)

OTHER PUBLICATIONS

Decision of Rejection dated Dec. 4, 2013 from corresponding Japanese Application No. 2009-552722.  
(Continued)

*Primary Examiner* — Jacqueline Stephens  
(74) *Attorney, Agent, or Firm* — Edgewell Personal Care Brands, LLC

(57) ABSTRACT

A tampon applicator barrel includes an insertion tip at a forward end of the barrel, a main body section that extends from the insertion tip, and a reverse taper section that is joined to the main body section so that the main body section is between the insertion tip and the reverse taper section. The main body section tapers toward the insertion tip section. The reverse taper section tapers in a direction away from the insertion tip section. A finger grip section extends from the reverse taper section to a plunger receiving end of the barrel opposite the forward end. The barrel is straight from the forward end to the plunger receiving end that receives a plunger.

30 Claims, 2 Drawing Sheets

Related U.S. Application Data

No. 13/669,840, filed on Nov. 6, 2012, now Pat. No. 9,421,135, which is a continuation of application No. 12/798,990, filed on Apr. 15, 2010, now Pat. No. 8,337,478, which is a continuation of application No. 10/242,474, filed on Sep. 12, 2002, now Pat. No. 7,727,208.

(58) Field of Classification Search
USPC ..... 604/367, 366, 359, 904, 385.17, 385.18, 604/285, 286, 11, 311
See application file for complete search history.

(56) References Cited

U.S. PATENT DOCUMENTS

| | | |
|---|---|---|
| 1,554,690 A | 9/1925 | Pride |
| 1,555,708 A | 9/1925 | Gale |
| 1,731,665 A | 10/1929 | Huebsch |
| 2,077,231 A | 4/1937 | Fourness et al. |
| 2,095,377 A | 10/1937 | Breese |
| 2,099,931 A | 11/1937 | Fourness |
| 2,123,750 A | 7/1938 | Schulz |
| 2,178,704 A | 11/1939 | Robinson |
| 2,222,088 A | 11/1940 | Petersen |
| 2,254,272 A | 9/1941 | Crockford |
| 2,301,868 A | 11/1942 | Gurley, Jr. et al. |
| 2,306,406 A | 12/1942 | Robinson |
| 2,330,257 A | 9/1943 | Bailey |
| 2,386,590 A | 10/1945 | Calhoun |
| 2,413,480 A | 12/1946 | Winter |
| 2,458,685 A | 1/1949 | Crockford |
| 2,476,956 A | 7/1949 | Bonham |
| 2,489,502 A | 11/1949 | Ruth |
| 2,409,414 A | 3/1950 | Rabell |
| 2,499,444 A | 3/1950 | Allison |
| 2,607,346 A | 8/1952 | Milcent |
| 2,706,986 A | 4/1955 | Carrier |
| 2,761,449 A | 9/1956 | Bletzinger |
| 2,799,055 A | 7/1957 | Carrier |
| 2,854,978 A | 10/1958 | Millman et al. |
| 2,877,767 A | 3/1959 | Schwartz |
| 3,204,635 A | 9/1965 | Voss et al. |
| 3,264,691 A | 8/1966 | Whitehead |
| 3,291,130 A | 12/1966 | Whitehead |
| 3,306,294 A | 2/1967 | Penska |
| 3,306,295 A | 2/1967 | Penska |
| 3,347,234 A | 10/1967 | Voss |
| 3,358,354 A | 12/1967 | Voss et al. |
| 3,369,544 A | 2/1968 | Crockford |
| 3,397,695 A | 8/1968 | Voss |
| 3,431,909 A | 3/1969 | Krusko |
| 3,431,910 A | 3/1969 | Kokx |
| 3,433,225 A | 3/1969 | Voss et al. |
| 3,520,302 A | 7/1970 | Jones |
| 3,570,489 A | 3/1971 | Brown |
| 3,572,341 A | 3/1971 | Glassman |
| 3,575,169 A | 4/1971 | Voss et al. |
| 3,595,236 A | 7/1971 | Corrigan |
| 3,606,643 A | 9/1971 | Mooney |
| 3,628,533 A | 12/1971 | Loyer |
| 3,643,661 A | 2/1972 | Crockford |
| 3,683,915 A | 8/1972 | Voss |
| 3,690,321 A | 9/1972 | Hirschman |
| 3,695,270 A | 10/1972 | Dostal |
| 3,699,965 A | 10/1972 | Dostal |
| 3,706,311 A | 12/1972 | Kokx et al. |
| 3,710,793 A | 1/1973 | Glassman |
| 3,712,305 A | 1/1973 | Wennerblom et al. |
| 3,726,277 A | 4/1973 | Hirschman |
| 3,731,687 A | 5/1973 | Glassman |
| 3,738,364 A | 6/1973 | Brien et al. |
| 3,762,413 A | 10/1973 | Hanke |
| 3,765,416 A | 10/1973 | Werner et al. |
| 3,794,029 A | 2/1974 | Dulle |
| 3,811,445 A | 5/1974 | Dostal |
| 3,812,856 A | 5/1974 | Duncan et al. |
| 3,834,389 A | 9/1974 | Dulle |
| 3,845,767 A | 11/1974 | Friese et al. |
| 3,856,013 A | 12/1974 | Dulle |
| 3,858,571 A | 1/1975 | Rudolph |
| 3,885,563 A | 5/1975 | Johnson et al. |
| 3,905,372 A | 9/1975 | Denkinger |
| 3,946,737 A | 3/1976 | Kobler |
| 3,954,104 A | 5/1976 | Kraskin et al. |
| 3,971,378 A | 7/1976 | Krantz |
| 3,981,305 A | 9/1976 | Ring |
| 3,983,873 A | 10/1976 | Hirschman |
| 3,994,298 A | 11/1976 | Des Marais |
| 4,010,751 A | 3/1977 | Ring |
| 4,018,255 A | 4/1977 | Diggs |
| 4,027,673 A | 6/1977 | Poncy et al. |
| 4,048,998 A | 9/1977 | Nigro |
| 4,077,408 A | 3/1978 | Murray et al. |
| 4,077,409 A | 3/1978 | Murray et al. |
| 4,099,976 A | 7/1978 | Kraskin et al. |
| 4,108,180 A | 8/1978 | Moehrle |
| D250,663 S | 12/1978 | Koch et al. |
| 4,175,467 A | 11/1979 | Lashley |
| 4,185,631 A | 1/1980 | McConnell |
| 4,186,742 A | 2/1980 | Donald |
| 4,198,978 A | 4/1980 | Nigro |
| 4,211,225 A | 7/1980 | Sibalis |
| 4,212,301 A | 7/1980 | Johnson |
| 4,217,900 A | 8/1980 | Wiegner et al. |
| 4,266,546 A | 5/1981 | Roland et al. |
| 4,271,835 A | 6/1981 | Conn et al. |
| 4,274,412 A | 6/1981 | Austin |
| 4,278,088 A | 7/1981 | Reeves et al. |
| 4,291,696 A | 9/1981 | Ring |
| 4,294,253 A | 10/1981 | Friese |
| 4,308,867 A | 1/1982 | Roseman et al. |
| 4,309,997 A | 1/1982 | Donald |
| 4,312,348 A | 1/1982 | Friese |
| 4,318,407 A | 3/1982 | Woon |
| 4,328,804 A | 5/1982 | Shimatani |
| 4,335,720 A | 6/1982 | Glassman |
| 4,335,721 A | 6/1982 | Matthews |
| 4,341,211 A | 7/1982 | Kline |
| 4,341,214 A | 7/1982 | Fries et al. |
| 4,351,339 A | 9/1982 | Sneider |
| 4,361,150 A | 11/1982 | Voss |
| 4,361,151 A | 11/1982 | Fitzgerald |
| 4,373,529 A | 2/1983 | Lilaonitkul et al. |
| 4,421,504 A | 12/1983 | Kline |
| 4,424,054 A | 1/1984 | Conn et al. |
| 4,424,370 A | 1/1984 | Keely |
| 4,475,911 A | 10/1984 | Gellert |
| D279,504 S | 7/1985 | Tump |
| 4,536,178 A | 8/1985 | Lichstein et al. |
| 4,543,086 A | 9/1985 | Johnson |
| 4,543,098 A | 9/1985 | Wolfe et al. |
| 4,553,965 A | 11/1985 | Conn et al. |
| D287,876 S | 1/1987 | Blatherwick et al. |
| 4,676,773 A | 6/1987 | Sheldon |
| 4,726,805 A | 2/1988 | Sanders, III |
| 4,743,237 A | 5/1988 | Sweere |
| 4,755,166 A | 7/1988 | Olmstead |
| 4,787,895 A | 11/1988 | Stokes et al. |
| 4,846,802 A | 7/1989 | Sanders, III |
| 4,881,644 A | 11/1989 | Norquest et al. |
| 4,891,042 A | 1/1990 | Melvin et al. |
| 4,973,302 A | 11/1990 | Armour et al. |
| 5,004,467 A | 4/1991 | Hinzmann et al. |
| 5,019,061 A | 5/1991 | Hoden et al. |
| 5,047,024 A | 9/1991 | Glassman |
| 5,084,038 A | 1/1992 | Sheldon et al. |
| 5,112,348 A | 5/1992 | Glassman |
| 5,133,457 A | 7/1992 | Kadel |
| 5,149,332 A | 9/1992 | Walton et al. |
| 5,153,971 A | 10/1992 | Van Iten |
| 5,158,535 A | 10/1992 | Paul et al. |
| 5,213,566 A | 5/1993 | Weissenburger |
| 5,267,953 A | 12/1993 | Paul et al. |
| 5,279,541 A | 1/1994 | Frayman et al. |

(56) References Cited

U.S. PATENT DOCUMENTS

| | | | |
|---|---|---|---|
| 5,290,501 A | 3/1994 | Klesius | |
| 5,342,331 A | 8/1994 | Silber et al. | |
| 5,350,371 A | 9/1994 | Van Iten | |
| 5,364,383 A | 11/1994 | Hayes et al. | |
| 5,370,633 A | 12/1994 | Villalta | |
| 5,387,206 A | 2/1995 | Valentine et al. | |
| 5,389,067 A | 2/1995 | Rejai | |
| 5,395,308 A | 3/1995 | Fox et al. | |
| 5,403,300 A | 4/1995 | Howarth | |
| 5,417,224 A | 5/1995 | Petrus et al. | |
| 5,437,628 A * | 8/1995 | Fox .................. A61F 13/26 604/1 | |
| 5,443,776 A | 8/1995 | Bartholomew et al. | |
| 5,445,605 A | 8/1995 | Pluss | |
| 5,542,914 A | 8/1996 | Van Iten | |
| 5,547,701 A | 8/1996 | Nielsen et al. | |
| 5,554,108 A | 9/1996 | Browning et al. | |
| 5,584,827 A | 12/1996 | Korteweg et al. | |
| 5,592,725 A | 1/1997 | Brinker | |
| 5,634,248 A | 6/1997 | McNelis et al. | |
| 5,659,934 A | 8/1997 | Jessup et al. | |
| 5,681,894 A | 10/1997 | Williams et al. | |
| 5,683,358 A | 11/1997 | Nielsen et al. | |
| 5,693,009 A | 12/1997 | Fox et al. | |
| 5,718,675 A | 2/1998 | Leijd | |
| 5,738,646 A | 4/1998 | Fox et al. | |
| 5,755,906 A | 5/1998 | Achter et al. | |
| 5,766,145 A | 6/1998 | Fox et al. | |
| 5,772,645 A | 6/1998 | Zadini et al. | |
| 5,782,794 A | 7/1998 | Assenheimer et al. | |
| 5,788,910 A | 8/1998 | McNelis et al. | |
| 5,792,096 A | 8/1998 | Rentmeester et al. | |
| 5,795,346 A | 8/1998 | Achter et al. | |
| 5,800,338 A | 9/1998 | Kollerup et al. | |
| 5,804,653 A | 9/1998 | Weng | |
| 5,807,372 A | 9/1998 | Balzar | |
| 5,817,047 A | 10/1998 | Osborn, III et al. | |
| 5,827,251 A | 10/1998 | Moder et al. | |
| 5,873,971 A | 2/1999 | Balzar | |
| 5,891,081 A | 4/1999 | McNelis et al. | |
| 5,891,123 A | 4/1999 | Balzar | |
| 5,891,127 A | 4/1999 | Moder et al. | |
| 5,911,712 A | 6/1999 | Leutwyler et al. | |
| 5,928,183 A | 7/1999 | Fox et al. | |
| 5,928,184 A | 7/1999 | Etheredge et al. | |
| 5,931,803 A | 8/1999 | Jackson | |
| 5,947,992 A | 9/1999 | Zadini et al. | |
| 5,954,683 A | 9/1999 | Downs et al. | |
| 5,964,741 A | 10/1999 | Moder et al. | |
| 5,986,000 A | 11/1999 | Williams et al. | |
| 5,986,165 A | 11/1999 | Moder et al. | |
| 6,003,216 A | 12/1999 | Hull, Jr. et al. | |
| 6,019,743 A | 2/2000 | Cole et al. | |
| 6,039,716 A | 3/2000 | Jessup et al. | |
| 6,039,828 A | 3/2000 | Achter et al. | |
| 6,045,526 A | 4/2000 | Jackson | |
| 6,068,899 A | 5/2000 | Osborn, III et al. | |
| 6,071,259 A | 6/2000 | Steiger et al. | |
| 6,090,038 A | 7/2000 | Zunker et al. | |
| 6,095,998 A | 8/2000 | Osborn et al. | |
| 6,095,999 A | 8/2000 | Jackson et al. | |
| 6,142,928 A | 11/2000 | Zunker et al. | |
| 6,177,606 B1 | 1/2001 | Etheredge et al. | |
| 6,177,608 B1 | 1/2001 | Weinstrauch | |
| 6,179,802 B1 | 1/2001 | Jackson | |
| 6,180,051 B1 | 1/2001 | Schoelling | |
| 6,183,436 B1 | 2/2001 | Korteweg et al. | |
| 6,186,994 B1 | 2/2001 | Bowles et al. | |
| 6,190,348 B1 | 2/2001 | Tiemann et al. | |
| 6,191,341 B1 | 2/2001 | Shippert | |
| 6,196,988 B1 | 3/2001 | Cole et al. | |
| 6,203,515 B1 | 3/2001 | Norquest et al. | |
| 6,206,867 B1 | 3/2001 | Osborn et al. | |
| 6,248,274 B1 | 6/2001 | Williams | |
| 6,254,565 B1 | 7/2001 | Williams et al. | |
| 6,254,566 B1 | 7/2001 | Buck et al. | |
| 6,264,626 B1 | 7/2001 | Linares et al. | |
| 6,270,470 B1 | 8/2001 | Buck et al. | |
| 6,283,952 B1 | 9/2001 | Child et al. | |
| 6,299,573 B1 | 10/2001 | Hull, Jr. et al. | |
| 6,302,861 B2 | 10/2001 | Tweddell, III et al. | |
| 6,302,862 B1 | 10/2001 | Osborn, III et al. | |
| 6,310,269 B1 | 10/2001 | Friese et al. | |
| 6,358,235 B1 | 3/2002 | Osborn, III et al. | |
| 6,368,442 B1 | 4/2002 | Linares et al. | |
| 6,380,455 B1 | 4/2002 | Moder et al. | |
| 6,416,488 B1 | 7/2002 | Jackson et al. | |
| 6,419,777 B1 | 7/2002 | Achter et al. | |
| 6,423,025 B1 | 7/2002 | Buzot | |
| 6,432,075 B1 | 8/2002 | Wada et al. | |
| 6,432,076 B1 | 8/2002 | Wada et al. | |
| 6,432,246 B1 | 8/2002 | Blake | |
| 6,450,986 B1 | 9/2002 | Binner et al. | |
| 6,465,713 B1 | 10/2002 | Gell et al. | |
| 6,478,764 B1 | 11/2002 | Suga | |
| D467,599 S | 12/2002 | Brazell | |
| 6,500,140 B1 | 12/2002 | Cole et al. | |
| 6,506,958 B2 | 1/2003 | Williams | |
| 6,508,780 B1 | 1/2003 | Edgett et al. | |
| 6,511,452 B1 | 1/2003 | Rejai et al. | |
| 6,545,283 B1 | 4/2003 | Williams et al. | |
| 6,570,052 B2 | 5/2003 | Zadini et al. | |
| 6,572,577 B1 | 6/2003 | Binner et al. | |
| D477,075 S | 7/2003 | Schoelling | |
| 6,585,300 B1 | 7/2003 | Rajala et al. | |
| 6,595,974 B1 | 7/2003 | Pauley et al. | |
| 6,603,054 B2 | 8/2003 | Chen et al. | |
| 6,610,025 B2 | 8/2003 | Berg et al. | |
| 6,635,205 B2 | 10/2003 | Williams et al. | |
| 6,645,136 B1 | 11/2003 | Zunker et al. | |
| 6,648,846 B2 | 11/2003 | Binner et al. | |
| 6,654,992 B2 | 12/2003 | Rajala et al. | |
| 6,673,032 B2 * | 1/2004 | Buzot .................. A61F 13/26 264/328.2 | |
| 6,685,787 B2 | 2/2004 | Linares et al. | |
| 6,685,788 B2 | 2/2004 | Linares et al. | |
| 6,719,743 B1 | 4/2004 | Wada | |
| 6,730,057 B2 | 5/2004 | Zhao et al. | |
| 6,740,070 B2 | 5/2004 | Agyapong et al. | |
| D492,033 S | 6/2004 | Jarmon | |
| 6,746,418 B1 | 6/2004 | Pauley et al. | |
| 6,756,434 B1 | 6/2004 | Williams et al. | |
| 6,773,423 B2 | 8/2004 | Osborn et al. | |
| 6,814,722 B2 | 11/2004 | Jackson et al. | |
| 6,830,554 B2 | 12/2004 | Jackson et al. | |
| 6,887,226 B2 | 5/2005 | Cassoni et al. | |
| 6,932,805 B2 | 8/2005 | Domeier et al. | |
| 6,958,057 B2 | 10/2005 | Berg et al. | |
| D511,832 S | 11/2005 | Bellofatto et al. | |
| D515,212 S | 2/2006 | Edgett et al. | |
| 7,044,928 B2 | 5/2006 | LeMay et al. | |
| 7,081,110 B2 | 7/2006 | Karapasha | |
| 7,098,292 B2 | 8/2006 | Zhao et al. | |
| 7,160,279 B2 | 1/2007 | Pauley et al. | |
| 7,172,573 B1 | 2/2007 | Lamb et al. | |
| 7,226,436 B2 | 6/2007 | Gorham et al. | |
| 7,250,129 B2 | 7/2007 | Williams et al. | |
| 7,335,194 B2 | 2/2008 | Wada | |
| 7,387,622 B1 | 6/2008 | Pauley et al. | |
| D572,362 S | 7/2008 | Edgett et al. | |
| D579,113 S | 10/2008 | Edgett et al. | |
| D612,940 S | 3/2010 | Edgett et al. | |
| 7,704,242 B2 | 4/2010 | LeMay et al. | |
| D626,650 S | 11/2010 | Edgett et al. | |
| D639,864 S | 6/2011 | Woelfel | |
| D652,848 S | 1/2012 | Flanagan et al. | |
| 8,198,504 B2 | 6/2012 | Glaug et al. | |
| 8,372,027 B2 | 2/2013 | LeMay et al. | |
| 8,444,590 B2 | 5/2013 | LeMay et al. | |
| 8,571,883 B2 | 10/2013 | Dougherty et al. | |
| 8,696,957 B2 | 4/2014 | Dougherty et al. | |
| 9,107,775 B2 | 8/2015 | Edgett et al. | |
| 2002/0010413 A1 | 1/2002 | Binner et al. | |
| 2002/0010447 A1 | 1/2002 | Williams et al. | |

(56) References Cited

U.S. PATENT DOCUMENTS

| | | |
|---|---|---|
| 2002/0038109 A1 | 3/2002 | Williams |
| 2002/0107497 A1 | 8/2002 | Osborn et al. |
| 2002/0133135 A1 | 9/2002 | Gell et al. |
| 2002/0143287 A1 | 10/2002 | Buzot |
| 2002/0143303 A1 | 10/2002 | Intravartolo et al. |
| 2002/0147436 A1 | 10/2002 | Gell et al. |
| 2002/0151859 A1 | 10/2002 | Schoelling |
| 2002/0156442 A1 | 10/2002 | Jackson et al. |
| 2002/0177835 A1 | 11/2002 | Zadini et al. |
| 2002/0183681 A1 | 12/2002 | Bernard |
| 2002/0188264 A1 | 12/2002 | Knuth et al. |
| 2002/0188283 A1 | 12/2002 | Binner et al. |
| 2003/0028176 A1 | 2/2003 | Berg et al. |
| 2003/0028177 A1 | 2/2003 | Berg et al. |
| 2003/0036721 A1 | 2/2003 | Zhao et al. |
| 2003/0040695 A1 | 2/2003 | Zhao et al. |
| 2003/0055391 A1 | 3/2003 | Nguyen et al. |
| 2003/0073948 A1 | 4/2003 | Binner et al. |
| 2003/0100871 A1 | 5/2003 | Mauro et al. |
| 2003/0105421 A1 | 6/2003 | Jarmon et al. |
| 2003/0125658 A1 | 7/2003 | Marvin |
| 2003/0135180 A1 | 7/2003 | Nguyen et al. |
| 2003/0149416 A1 | 8/2003 | Cole et al. |
| 2003/0158533 A1 | 8/2003 | Agyapong et al. |
| 2003/0163080 A1 | 8/2003 | LeMay et al. |
| 2003/0167048 A1 | 9/2003 | Policappelli |
| 2003/0172504 A1 | 9/2003 | Sageser et al. |
| 2003/0176844 A1 | 9/2003 | Randall et al. |
| 2003/0176845 A1 | 9/2003 | Kollwitz et al. |
| 2003/0208179 A1 | 11/2003 | Fuchs et al. |
| 2003/0208180 A1 | 11/2003 | Fuchs et al. |
| 2003/0216680 A1 | 11/2003 | Binner et al. |
| 2003/0236485 A1 | 12/2003 | Fedyk et al. |
| 2004/0000222 A1 | 1/2004 | Rejai et al. |
| 2004/0010220 A1 | 1/2004 | Miller et al. |
| 2004/0054317 A1 | 3/2004 | LeMay et al. |
| 2004/0064082 A1 | 4/2004 | LeMay et al. |
| 2004/0153024 A1 | 8/2004 | Pauley et al. |
| 2004/0193131 A1 | 9/2004 | Wada |
| 2004/0199100 A1 | 10/2004 | LeMay et al. |
| 2004/0199101 A1 | 10/2004 | LeMay et al. |
| 2004/0199102 A1 | 10/2004 | LeMay et al. |
| 2004/0225269 A1 | 11/2004 | Zhao et al. |
| 2004/0243088 A1 | 12/2004 | LeMay et al. |
| 2005/0015041 A1 | 1/2005 | Karapasha |
| 2005/0020964 A1 | 1/2005 | Melvin et al. |
| 2005/0022349 A1 | 2/2005 | Pham et al. |
| 2005/0070839 A1 | 3/2005 | Jackson et al. |
| 2005/0080393 A1 | 4/2005 | Policappelli |
| 2005/0096617 A1 | 5/2005 | Gorham et al. |
| 2005/0096619 A1 | 5/2005 | Costa |
| 2005/0177091 A1 | 8/2005 | Jarmon et al. |
| 2007/0026228 A1 | 2/2007 | Hartmann et al. |
| 2007/0156081 A1 | 7/2007 | Karapasha |
| 2007/0232982 A1 | 10/2007 | Jarmon et al. |
| 2007/0260211 A1 | 11/2007 | Schmidt-Forst |
| 2007/0276317 A1 | 11/2007 | Henderson et al. |
| 2007/0293809 A1 | 12/2007 | Karapasha |
| 2008/0033337 A1 | 2/2008 | Dougherty et al. |
| 2008/0058751 A1 | 3/2008 | Edgett et al. |
| 2008/0119778 A1 | 5/2008 | Jorgensen et al. |
| 2008/0132868 A1 | 6/2008 | Jorgensen et al. |
| 2008/0167597 A1 | 7/2008 | Dougherty |
| 2008/0221502 A1 | 9/2008 | Binner et al. |
| 2008/0287902 A1 | 11/2008 | Edgett et al. |
| 2009/0036859 A1 | 2/2009 | Dougherty et al. |
| 2009/0156979 A1 | 6/2009 | Andersch |
| 2009/0227975 A1 | 9/2009 | Dougherty et al. |
| 2009/0234268 A1 | 9/2009 | Jorgensen et al. |
| 2009/0247981 A1 | 10/2009 | Glaug et al. |
| 2009/0281474 A1 | 11/2009 | Dougherty et al. |
| 2009/0281514 A1 | 11/2009 | Dougherty et al. |
| 2010/0036309 A1 | 2/2010 | Jorgensen et al. |
| 2010/0120707 A1 | 5/2010 | Dougherty et al. |
| 2010/0198133 A1 | 8/2010 | Dougherty et al. |
| 2012/0061867 A1 | 3/2012 | Dougherty et al. |

FOREIGN PATENT DOCUMENTS

| | | |
|---|---|---|
| BE | 758152 | 4/1971 |
| CA | 11086099 | 9/1980 |
| CA | 1110401 | 10/1981 |
| CA | 2024473 | 3/1991 |
| CA | 2095390 | 11/1993 |
| CA | 2143083 | 2/1996 |
| CA | 2145692 | 2/1996 |
| CA | 2153818 | 2/1996 |
| CA | 2280251 | 2/2000 |
| CA | 2302065 | 9/2000 |
| CA | 2325269 | 5/2001 |
| CA | 2325669 | 5/2001 |
| CA | 108982 S | 8/2006 |
| CA | 115880 S | 8/2008 |
| CA | 2441647 C | 5/2009 |
| DE | 1920773 | 12/1969 |
| DE | 3328910 | 2/1985 |
| DE | 3540725 | 5/1986 |
| DE | 3726311 | 2/1989 |
| DE | 4446226 | 6/1995 |
| DE | 19726648 | 12/1998 |
| EP | 110793 | 12/1983 |
| EP | 158543 | 3/1985 |
| EP | 0243250 | 10/1987 |
| EP | 546256 | 7/1992 |
| EP | 797971 | 10/1997 |
| FR | 1515087 | 3/1968 |
| FR | 2567399 | 7/1984 |
| GB | 2097259 | 11/1982 |
| GB | 8428462 A | 12/1984 |
| GB | 9419135 | 11/1994 |
| GB | 2414394 B | 1/2006 |
| GB | 2415626 B | 3/2006 |
| IL | 154877 | 7/2009 |
| IL | 163734 | 12/2009 |
| JP | H05-68695 | 3/1993 |
| JP | 10024064 | 1/1998 |
| JP | 2000288018 | 10/2000 |
| JP | 2001-008964 | 1/2001 |
| JP | 200117465 | 1/2001 |
| JP | 2001145658 | 5/2001 |
| JP | 2005-526584 | 9/2005 |
| JP | HO62-027952 | 9/2005 |
| JP | 2005531345 | 10/2005 |
| WO | 8000008 | 1/1980 |
| WO | 93/08779 | 5/1993 |
| WO | 94/15564 | 7/1994 |
| WO | 9605795 | 2/1996 |
| WO | 9637173 | 11/1996 |
| WO | 9640032 | 12/1996 |
| WO | 9806366 | 2/1998 |
| WO | 9900097 | 1/1999 |
| WO | 0037013 | 6/2000 |
| WO | 0066213 | 11/2000 |
| WO | 0197735 | 12/2001 |
| WO | 0200153 | 1/2002 |
| WO | 0202176 | 1/2002 |
| WO | 0226159 | 4/2002 |
| WO | 02074352 | 9/2002 |
| WO | 03032883 | 4/2003 |
| WO | 03101362 A2 | 11/2003 |
| WO | 04000160 | 12/2003 |
| WO | 2005112856 A1 | 12/2005 |
| WO | 2005112862 A1 | 12/2005 |
| WO | 2006016933 A1 | 2/2006 |
| WO | 2006037157 | 4/2006 |
| WO | 2004/098449 | 11/2006 |
| ZA | 9305011 | 2/1994 |

OTHER PUBLICATIONS

Official Action dated Jan. 22, 2012 from corresponding Mexican Application No. MX/a/2009/009468.

(56) References Cited

OTHER PUBLICATIONS

Decision of Rejection mailed Dec. 11, 2012 from corresponding Japanese Application No. 2009-552722.
Official Action dated Jan. 22, 2013 from corresponding Mexican Application No. MX/a/2009/009468.
Official Notice of Final Rejection Dated Feb. 27, 2012 From Korean Application No. 10-2009-7020746.
Notice of Notice of Reasons for Rejection dated Feb. 20, 2012 from Japanese Application No. 2009-552722.Reasons for Rejection dated Feb. 20, 2012 from Japanese Application No. 2009-552722.
Canadian Office Action dated Apr. 6, 2011 for corresponding Canadian Patent Application No. 2.680.144.
Office Action dated Jun. 14, 2011 from Korean Patent Application No. 10-2009-7020746.
Official Notice dated Aug. 2, 2012 from Korean Application No. 10-2009-7020746.
Notification of the First Office Action dated Apr. 6, 2012 from Chinese Application No. 200880014388.
Korean Office Action dated Aug. 2, 2012 for corresponding Korean Patent Application No. 10-2009-7020746 with English stunmary.
European Search Report dated Apr. 27, 2011 for corresponding European Patent Application No. 047606017.
English translation of First Office Action dated Apr. 6, 2012 for corresponding Chinese Patent Application No. 200880143883.
Office Action and English summary of Office Action previously cited on Sep. 14, 2012.
Notification of the Second Office Action dated Nov. 30, 2012 from corresponding Chinese Application No. 2008800143883.
Supplementary European Search Report dated Dec. 17, 2012 from corresponding European Application No. 087264628.
Israeli Office Action for corresponding Israeli Patent Application No. 200734 with English summary dated Apr. 5, 2011.
Photocopy of box panels for QB. Silk Ease. Personal Fit Protection.
International Search Report from PCT Application No. PCT/US2008/02934. dated Jul. 14, 2008.
Written Opinion from PCT Application No. PCT/US2008/02934, dated Jul. 14, 2008.
Examination Report dated Aug. 25, 2011 from corresponding European Patent Application No. 04 760 601.7-1217.
"Retrieved from the internet on Mar. 3, 2010: http://www.inerriamwebstercom'dictionary/slit.""".
Canadian Examination Report Dated Oct. 7, 2009, from corresponding Application No. 2,498,508.
Canadian Examination Report Dated Dec. 18, 2008, from corresponding Application No. 2,498,508.
Canadian Examination Report Dated Jan. 15, 2008, from corresponding Application No. 2,498,508.
Canadian Examnation Report Dated May 3, 2008, from corresponding Application No. 2,498,508.
Notice of Reasons for Rejection Dated Aug. 5, 2008, from corresponding Japanese Application No. 2004-536364.
Final Notice of Rejection Dated May 12, 2009, from corresponding Japanese Application No. 2004-027399.
Official Action Dated Apr. 26, 2005, from corresponding Japanese Application No. 2004-27406.
Notice of Reasons for Rejection Dated Oct. 4, 2011, from corresponding Japanese Application No. 2009/209408.
Official Action received Jul. 2, 2010, from corresponding Mexican Application No: Pa/a/2005/002767.
Official Action received Nov. 26, 2010, from corresponding Mexican Application No. PA/a/2005/002767.
Official Action Received Feb. 16, 2011, from corresponding Mexican Application No. Pa/a/2005/002767.
US Office Action Dated Jun. 26, 2007, from corresponding U.S. Appl. No. 29/205,148.
US Office Action Dated Jun. 3 2005, from corresponding U.S. Appl. No. 29/205,148.
US Office Action Dated May 16, 2005, from corresponding U.S. Appl. No. 29/201,235.
US Office Action Dated Oct. 1, 2007, from corresponding U.S. Appl. No. 29/201,242.
US Office Action Dated Aug. 25, 2005, from corresponding U.S. Appl. No. 29/201,242.
US Office Action Dated Jul. 2, 2007, from corresponding U.S. Appl. No. 29/201,242.
US Office Action Dated Jun. 9, 2009, from corresponding U.S. Appl. No. 10/242,474.
US Office Action dated Dec. 16, 2008, from corresponding U.S. Appl. No. 10/242,474.
US office Action Dated May 5, 2008, from corresponding U.S. Appl. No. 10/242,474.
US Office Action Dated Dec. 20, 2006, from corresponding U.S. Appl. No. 10/242,474.
US Office Action Dated Jun. 16, 2006, from corresponding U.S. Appl. No. 10/242,474.
US Office Action dated May 20, 2004, from corresponding U.S. Appl. No. 10/242,474.
US Office Action Dated Jan. 12, 2004, from corresponding U.S. Appl. No. 10/242,474.
US Office Action Dated Mar. 10, 2005, from corresponding U.S. Appl. No. 10/242,474.
US Office Action Dated Feb. 8, 2005, from corresponding U.S. Appl. No. 10/242,474.
US Office Action Dated Nov. 17, 2004, from corresponding U.S. Appl. No. 10/242,474.
US Office Action Dated Dec. 30, 2005, from corresponding U.S. Appl. No. 10/242,474.
2005 Gentle Glide Plastic Tampons.

\* cited by examiner

ERGONOMIC TAMPON APPLICATOR

CROSS-REFERENCE TO RELATED APPLICATIONS

This is a continuation application of U.S. patent application Ser. No. 14/576,473, filed on Dec. 19, 2014, which is a continuation application of U.S. patent application Ser. No. 13/669,840 filed Nov. 6, 2012, which is a continuation application of U.S. patent application Ser. No. 12/798,990, filed Apr. 15, 2010, which is a continuation application of U.S. patent application Ser. No. 10/242,474, filed Sep. 12, 2002, claims the benefit of priority from U.S. Provisional patent application Ser. No. 60/499,443, filed on 2 Sep. 2003. Each of the above-noted applications is incorporated herein by reference.

BACKGROUND OF THE INVENTION

A. Field of Endeavor

The disclosure relates generally to an improved tampon or tampon applicator. More particularly, the present disclosure relates to a tampon applicator with a barrel that has a reverse taper section for improved ease of use and user comfort.

B. Description of the Prior Art

Commercial tampon applicators typically consist of a barrel and a plunger used to expel an absorbent pledget housed in the barrel. The barrel is typically sub-divided into three sections, namely a finger grip, an insertion tip, and a main body section, which is located between the finger grip and insertion tip sections.

The finger grip section is typically the same diameter as the main body section of the barrel, but some designs (e.g., Playtex® Gentle Glide®) have a reduced diameter grip for improve grippability. The main body section is typically linear, except on plastic molded barrels where there is a slight taper to improve release characteristics from the manufacturing mold. The insertion tip section on some types of barrels have "petals" which curve over and enclose the pledget (i.e., rounded tip) housed in the barrel, but readily flex outwardly as the pledget is expelled through the insertion tip.

SUMMARY OF THE INVENTION

The present disclosure provides a tampon applicator that is ergonomic.

The present disclosure also provides such an ergonomic tampon applicator with a plunger and a barrel.

The present disclosure further provides such an ergonomic tampon applicator barrel having a finger grip section, a reverse taper section, a main body section and an insertion tip section.

The present disclosure still further provides such an ergonomic tampon applicator barrel reverse taper section where the reverse taper is towards the finger grip section.

The present disclosure also provides such an ergonomic tampon applicator barrel finger grip section having a finger accepting region.

The present disclosure further provides such an ergonomic tampon applicator insertion tip section formed with a plurality of petals.

The present disclosure still further provides such an ergonomic tampon applicator main body section with a maximum diameter section that is sensually perceivable to a user to alert the user to the proper insertion depth of the applicator.

The present disclosure also provides such an ergonomic tampon applicator having a plunger with at least one flared end.

These and other objects and advantages of the present disclosure will be appreciated from an ergonomically improved tampon applicator having a plunger and a barrel, of the present disclosure. The barrel has four distinct sections, namely a finger grip section, a reverse taper section, a main body section, and an insertion tip section. The reverse taper section is tapered towards the fingergrip section, and the main body section is tapered in an opposite direction towards the insertion tip section. A maximum diameter is formed where the reverse taper section and main body section meet on the barrel. The maximum diameter provides a sensory indicator to the user to alert the user when the applicator has been inserted to the proper depth in the vagina.

DETAILED DESCRIPTION OF THE INVENTION

Figure 1:
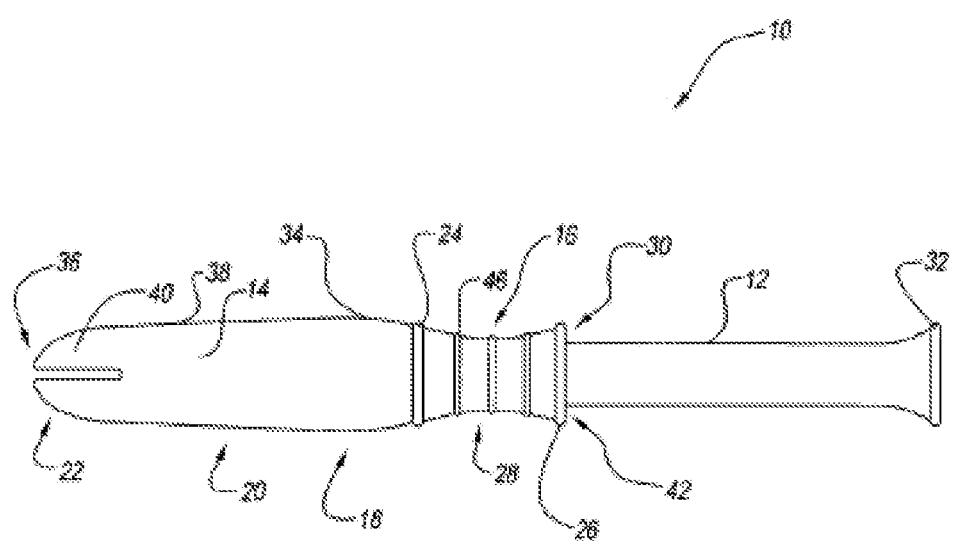
FIG. 1 is a plan view of a tampon applicator of the present disclosure.

Referring to FIG. 1, drawings and, in particular, FIG. 1, there is shown an ergonomically improved tampon applicator according to the present disclosure generally represented by reference numeral 10. The ergonomically improved applicator 10 is easier to use and more comfortable to insert and remove. Applicator 10 includes a plunger 12 and a barrel 14.

Barrel 14 may be divided into four sections, as opposed to three sections typically found in prior art tampon applicators. The four sections include a finger grip section 16, a reverse taper section 18, a main body section 20, and an insertion tip section 22.

Finger grip section 16 is bound by a forward edge ridge 24 and a rearward edge ridge 26. Forward edge ridge 24 provides a firm grip surface during insertion of applicator 10 into the vaginal vault. Rearward edge ridge 26 provides a firm grip surface during expulsion of the pledget (not shown) and during removal of applicator 10 from the body. Forward and rearward edge ridges 24, 26 are about 6 mm to about 22 mm in diameter. Preferably, the forward and rearward edges 24, 26 are about 11 mm to about 17 mm in diameter, with about 14 mm being the most preferred diameter.

A finger accepting region 28 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart. More preferably, forward edge ridge 24 and rearward edge ridge 26 are spaced about 17 mm to about 21 mm apart, with about 19 mm being the most preferred spacing. Finger accepting region 28 may be concave, convex, flat, or any combinations thereof. Preferably, region 28 is concave, which conforms to the contour of a user's finger. The maximum diameter of region 28 is preferably slightly less than the diameter of edge ridges 24, 26.

Preferably, region 28 has a maximum to minimum diameter ratio of about 1.10 to about 1.75, with a more preferred ratio of about 1.25 to about 1.35.

Finger accepting region 28 may also include one or more gripping structures 46 to improve grippability of applicator 10. Suitable gripping structures 46 include, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 14 occurs at the forward end of reverse taper section 18. Reverse taper is meant to include a taper in the reverse direction, i.e. in a direction away from the insertion end of applicator 10, but not necessarily the same dimensional taper as main body section 20. The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 14 exerts a slightly greater pressure than the smaller diameter portions of the barrel on the vaginal opening. This unique feature of barrel 14 provides a sensually perceivable way of signaling or indicating to a user that applicator 10 has been inserted to the correct depth in the vagina. Thus, the location of maximum diameter 34 along the length of barrel 14 is a critical aspect of the present disclosure. The location of maximum diameter 34 on barrel 14 is about 32 mm to about 54 mm in the axial direction of barrel 14 from forward end 36 of insertion tip 22. Preferably maximum diameter 34 is located about 40 mm to about 50 mm, and more preferably about 44 mm in the axial direction of barrel 14 from forward end 36 of insertion tip 22.

Main body section 20 is joined to reverse taper section 18 where maximum diameter 34 of barrel 14 is located. Main body section 20 tapers toward insertion tip section 22 in either a linear or curvilinear fashion so that its smallest diameter occurs where main body section 20 meets insertion tip section 22. The ratio of maximum diameter 34 to the diameter at the forward end 38 of main body section 20 is about 1.1 to about 1.5, and more preferably about 1.2 to about 1.3. This tapering of main body section 20 facilitates insertion comfort by gradually parting the vulva-vaginal channel over a longer length than that of only insertion tip section 22.

Insertion tip section 22 begins where there is a substantial change in the curvature of the forward portion of the barrel that is where the pledget-enclosing petals 40 are formed. In applicator designs where no petals are used, insertion tip 22 is the forward edge of the main body section 20 of barrel 14. The preferred insertion tip 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a horizontal axis of applicator 10, is about 0.9 to about 1.8, and more preferably about 1.1 to about 1.3.

The less severe curvature of insertion tip section 22 also facilitates insertion comfort by gradually parting the vulva-vaginal channel along its longer length.

It should be understood that while tampon applicator barrel 14 of the present disclosure is depicted as having four sections, namely a finger grip section, a reverse taper section, a main body section, and an insertion tip section, the tampon applicator barrel can include a reverse taper section and at least one additional section selected from a finger grip section, a main body section, an insertion tip section, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Figure 2:
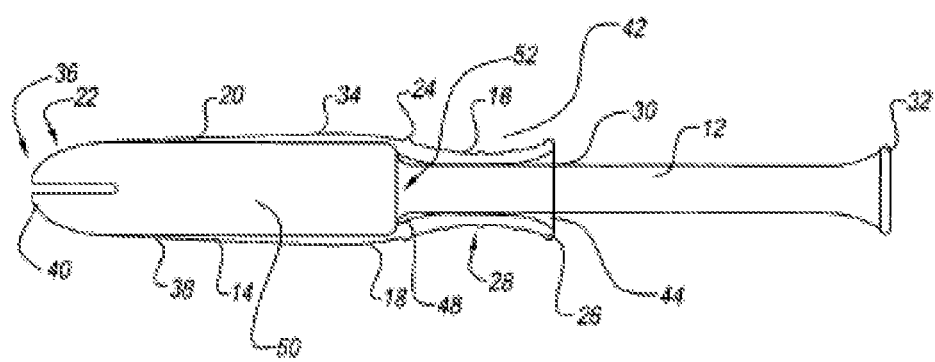
FIG. 2 is a cut away view of the tampon applicator of FIG. 1 depicting an absorbent pledget housed in the barrel.
Figure 3:
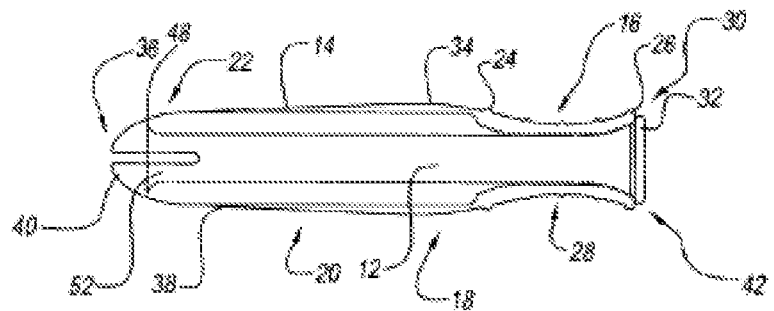
FIG. 3 is a cut away view of the tampon applicator of FIG. 2 after the pledget has been expelled from the barrel.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of finger receiving region 28 so that plunger 12 telescopically fits throughout the interior of barrel 14. Preferably, in one embodiment of the present disclosure, plunger 12 has a diameter about 4 mm to about 18 mm. More preferably, plunger 12 has a diameter about 5 mm to about 9 mm with the most preferred diameter being about 7 mm.

Plunger 12 has a first flare 32 at its distal end and a second flare or retaining structure 48 at its opposite barrel end 52. Finger grip section 16 has a plunger receiving end 30. Plunger receiving end 30 of finger grip section 16 has a chamfer 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator. Such an ergonomic applicator is conducive to one handed use, since the distance between finger grip section 16 and first flare 32, where the fingertip is placed, is reduced by an amount equal to the length of first flare 32. Second flare or retaining feature 48 on barrel end 52 of plunger 12 prevents separation from barrel 14.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The pledget housed by applicator barrel 14 preferably has a tapered forward end that corresponds to that of insertion tip 22. The matching taper supports petals 40 during insertion of applicator 10 so that the petals cannot flex out of shape, thus enhancing comfort. Additionally, during expulsion from applicator 10, the pledget's tapered tip will gradually part the vaginal channel, further enhancing user comfort.

Suitable materials for forming plunger 12 and/or barrel 14 include, for example, biopolymer, cardboard, heat shrink plastic, paper slurry, plastic, plastic tubing, pulp slurry, pulp-molded paper, or any combinations thereof.

To reduce friction and/or increase strength, plunger 12 and/or barrel 14 may be coated with a coating material. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

The foregoing specification and drawings are merely illustrative of the present invention and are not intended to limit the invention to the disclosed embodiments. Variations and changes, which are obvious to one skilled in the art, are intended to be within the scope and nature of the present invention, which is defined in the appended claims.

The invention claimed is:

1. A tampon assembly, comprising:
an applicator barrel having an internal cavity and a substantially straight central axis, the applicator barrel including:
an insertion tip section having a forward end, the insertion tip section having a curved tapered shape along the central axis in which a ratio of a maximum diameter of the insertion tip to a length of the insertion tip is in a range from about 0.9 to about 1.8, the insertion tip having between three and eight petals;
a main body section adjacent to the insertion tip section and opposite of the forward end of the insertion tip section, the main body section having a maximum diameter of the applicator barrel;
a reverse taper section adjacent to the main body section, the reverse taper section tapering downwardly in a direction away from the insertion tip section;
a finger grip section adjacent to the reverse taper section and being bound by a forward edge and a rearward edge, the reverse taper section tapering downwardly to a diameter that is slightly less than a diameter of the forward edge, the finger grip section having a concave shape between the forward edge and the rearward edge and including a plurality of protruding ribs extending away from a surface of the finger grip section between the forward edge and the rearward edge, the plurality of protruding ribs having a height that is less than the height of the forward edge, the rearward edge and the maximum diameter of the applicator barrel, the finger grip section including an opening leading into the internal cavity, the internal cavity within the finger grip section being defined by a wall adjacent to the opening,
wherein the insertion tip section, the main body section, the reverse taper section and the finger grip section are unitary and are all coaxially positioned around the central axis of the applicator barrel; and
a pledget within the internal cavity of the applicator barrel, the pledget including a tapered forward end for supporting the petals during the insertion of the applicator barrel into a vagina; and
a plunger that telescopically extends into the internal cavity of the applicator barrel through the opening at the finger grip section, the plunger including a distal end to be pushed forwardly toward the internal cavity along the central axis, the distal end including a flared region that is received within the wall of the internal cavity while a proximal end of the plunger is located in the insertion tip region expelling the pledget through the petals.

2. The tampon applicator according to claim 1, wherein the insertion tip section has a curvature along the central axis that at least partially approximates at least one of an elliptical curved tapered shape and a hyperbolic curved tapered shape.

3. The tampon assembly of claim 1, wherein the tapered forward end of the pledget has a tapered shape that matches the curved tapered shape of the petals.

4. The tampon assembly of claim 1, wherein the concave shape of the finger grip section results in a ratio of the maximum diameter of the finger grip section to the minimum diameter of the finger grip section is about 1.1 to about 1.75.

5. The tampon assembly of claim 1, wherein the ratio of the maximum diameter of the insertion tip to the length of the insertion tip is about 1.1 to about 1.3.

6. The tampon assembly of claim 1, wherein the maximum diameter of the applicator barrel is located within the main body section directly adjacent to the reverse taper section.

7. The tampon assembly of claim 1, wherein the distance between the forward edge and the rearward edge of the finger grip section is between about 13 mm and about 40 mm.

8. The tampon assembly of claim 7, wherein the distance between the forward edge and the rearward edge of the finger grip section is between about 17 mm to about 21 mm.

9. The tampon assembly of claim 1, wherein a rearward end of the flare on the plunger is between about 12 mm and about 16 mm, wherein the flare is smaller in diameter than the rearward edge of the finger grip.

10. The tampon assembly of claim 1, wherein the reverse taper section begins about 50 to about 54 mm from the forward end of insertion tip section.

11. The tampon assembly of claim 1, wherein maximum diameter on the barrel is between about 32 mm and about 54 mm from the forward end of insertion tip section.

12. The tampon assembly of claim 7, wherein the tapered forward end of the pledget has a tapered shape that matches the curved tapered shape of the petals.

13. The tampon applicator of claim 7, wherein at least one of the plurality of gripping structures encircles the surface of the finger grip section.

14. A tampon assembly, comprising:
a plastic applicator barrel having an internal cavity and a substantially straight central axis, the applicator barrel including:
an insertion tip section having between three and eight petals, wherein the petals have a curvature along the central axis that at least partially approximates at least one of an elliptical curved tapered shape and a hyperbolic curved tapered shape;
a main body section adjacent the insertion tip, the main body section having a maximum diameter of the applicator barrel;
a reverse taper section adjacent to the body section, the reverse taper section tapering downwardly in a direction away from the insertion tip;
a finger grip section adjacent to the reverse taper section and being bound by a forward edge and a rearward edge, the reverse taper section tapering downwardly to a diameter that is slightly less than a diameter of the forward edge, the finger grip section having a concave shape between the forward edge and a rearward edge and including a plurality of gripping structures extending away from a surface of the finger grip section between the forward edge and the rearward edge, the plurality of gripping structures having a height that is less than the height of forward edge, the rearward edge and the maximum diameter of the applicator barrel, the finger grip section including an opening leading into the internal cavity, the internal cavity within the finger grip section being defined by a wall adjacent to the opening, the finger grip section having a generally circular cross-sectional shape; and wherein the insertion tip section, the main body section, the reverse taper section and the finger grip section are unitary and are all coaxially positioned around the central axis of the applicator barrel; and a pledget within the internal cavity of the applicator barrel, the pledget including a tapered forward end along the central axis for supporting the petals during use of the tampon assembly; and a plunger that telescopically extends into the internal cavity of the applicator barrel through the opening at the finger grip section, the plunger including a distal end to be pushed forwardly toward the internal cavity, the plunger having a generally circular cross-sectional shape, the plunger having an outer diameter that is slightly smaller than a smallest diameter of the finger grip section such that the plunger generally telescopically fits into the finger grip section.

15. The tampon assembly of claim 14, wherein the outer diameter of the plunger is about 7 mm.

16. The tampon assembly of claim 15, wherein a rear flared region of the plunger has a diameter of about 12 mm.

17. A tampon assembly, comprising:

a plastic applicator barrel having an internal cavity and a substantially straight central axis, the applicator barrel including:

an insertion tip section having a generally curved tapered shape along the central axis, the insertion tip having between three and eight petals;

a main body section adjacent the insertion tip section such that the petals converge at the main body section, the main body section having a maximum diameter of the applicator barrel;

a reverse taper section adjacent to the body section, the reverse taper section tapering downwardly in a direction away from the insertion tip;

a finger grip section adjacent to the reverse taper section and being bound by a forward edge and a flared rearward edge, the reverse taper section tapering downwardly to a diameter that is slightly less than a diameter of the forward edge, the finger grip section having a concave shape between the forward edge and a rearward edge and including a plurality of gripping structures extending away from a surface of the finger grip section between the forward edge and the rearward edge, the finger grip section including an opening leading into the internal cavity, the finger grip section having a diameter that is less than the maximum diameter of the main body section, the internal cavity within the finger grip section being defined by a wall adjacent to the opening, the finger grip section having a generally circular cross-sectional shape; and wherein the insertion tip section, the main body section, the reverse taper section and the finger grip section are unitary and are all coaxially positioned around the central axis of the applicator barrel; and a pledget within the internal cavity of the applicator barrel, the pledget including a tapered forward end for supporting the petals during use of the tampon assembly; and a plunger having an outer diameter that is slightly smaller than and fits within an internal diameter within the finger grip section such that the plunger telescopically extends into the internal cavity of the applicator barrel through the opening at the finger grip section, the plunger including a distal end to be pushed forwardly toward the internal cavity, the plunger having a barrel end opposite to the distal end, the distal end having a flare that is smaller in diameter than the flared rearward edge of the finger grip section, and wherein the rearward edge receives the distal end of the plunger permitting shortening of the length of the plunger protruding from the barrel as the length of the plunger is available for telescopically fitting into the applicator barrel.

18. The tampon applicator according to claim 17, wherein the insertion tip section has a curvature that at least partially approximates at least one of an elliptical curved tapered shape and a hyperbolic curved tapered shape.

19. The tampon assembly of claim 17, wherein the tapered forward end of the pledget has a tapered shape that matches the curved tapered shape of the petals.

20. The tampon assembly of claim 17, wherein the tapered forward the of the pledget is curved, elliptical, hyperbolic, or combinations thereof.

21. The tampon assembly of claim 17, wherein the barrel end has a chamfer to receive a retaining feature during pledget expulsion, thereby permitting shortening of the length of the plunger protruding from the barrel.

22. The tampon assembly of claim 17, wherein the flare of the distal end of the plunger has a maximum diameter of about 6 mm to about 22 mm.

23. The tampon assembly of claim 22, wherein the flare of the distal end of the plunger has the maximum diameter of about 12 mm to about 16 mm, wherein the flare is smaller in diameter than the rearward edge of the finger grip.

24. The tampon assembly of claim 17, wherein the concave shape of the finger grip section comprises one or more flat portions.

25. A tampon assembly, comprising:

an applicator barrel having a substantially straight central axis and an internal cavity, including:

an insertion tip section having a curved tapered shape along the central axis in which a ratio of a maximum diameter of the insertion tip to a length of the insertion tip is in a range from about 1.1 to about 1.3, the insertion tip having between three and eight petals;

a main body section adjacent the insertion tip, the main body section having a maximum diameter of the applicator barrel;

a reverse taper section adjacent to the body section, the reverse taper section tapering downwardly in a direction away from the insertion tip;

a finger grip section adjacent to the reverse taper section and being bound by a forward edge and a rearward edge, the finger grip section having a concave shape between the forward edge and a rearward edge such that a middle region of the finger grip section has a minimum diameter of the finger-grip region, the finger grip region including a plurality of protruding ribs extending away from a surface of the finger grip section between the forward edge and the rearward edge, the finger grip section including an opening at the rearward edge leading into the internal cavity, the plurality of protruding ribs having a height that is less than the height of forward edge, the rearward edge and the maximum diameter of the applicator barrel, the plurality of ribs encircling the finger grip section and extending in series along the length of the concave finger grip region, the internal cavity within the finger-grip section being defined by a chamfered wall adjacent to the opening that tapers downwardly in diameter from the rearward edge toward the middle region, the finger grip section having a ratio of a maximum diameter of the finger grip section to the minimum diameter of the finger grip section of about 1.25 to about 1.35; and a pledget within the internal cavity of the applicator barrel, the pledget including a tapered forward end for supporting the petals during the insertion of the applicator barrel into a vagina; and a plunger that telescopically extends into the internal cavity of the applicator barrel through the opening at the finger grip section, the plunger including a distal end section that is moved forwardly toward the internal cavity and a front end section within the internal cavity of the applicator barrel for engaging the pledget, the front end section includes a front terminal end and a front flared region that tapers downwardly toward the distal end section, the distal end section includes a rear terminal end and a rear flared region that tapers downwardly toward the front section, the rear flared region having an outer diameter of about 12 mm to about 16 mm, and wherein as the plunger expels the pledget through the petals, the rear flared region is received by the chamfered wall of the internal opening of the applicator barrel and the rear terminal end of the distal end section of the plunger is stopped from entering the internal opening of the finger grip section, wherein the insertion tip section, the main body section, the reverse taper section and the finger grip section are unitary and are all coaxially positioned around the central axis of the applicator barrel.

26. The tampon assembly of claim 25, wherein the tapered forward end of the pledget has a tapered shape that matches the curved tapered shape of the petals.

27. The tampon assembly of claim 25, wherein the maximum diameter of the applicator barrel is located within the main body section directly adjacent to the reverse taper section.

28. The tampon assembly of claim 25, wherein the main body section includes a linear tapered portion or a curvilinear tapered portion extending from the maximum diameter toward the insertion tip section.

29. The tampon assembly of claim 25, wherein an outer diameter of the plunger is about 7 mm and the inner diameter of the finger grip section is slightly larger than the outer diameter of the plunger.

30. The tampon assembly of claim 25, wherein the concave shape of the finger grip section comprises one or more flat portions.

* * * * *